US00RE43764E

(19) United States
(12) Reissued Patent
De Ferra et al.

(10) Patent Number: US RE43,764 E
(45) Date of Reissued Patent: Oct. 23, 2012

(54) PURIFYING PROCESS FOR PHOSPHATIDYLSERINE

(75) Inventors: Lorenzo De Ferra, Rome (IT); Pietro Massardo, Rome (IT)

(73) Assignee: Chemi S.p.A. (IT)

(21) Appl. No.: 13/167,785

(22) Filed: Jun. 24, 2011

Related U.S. Patent Documents

Reissue of:
(64) Patent No.: 6,645,742
Issued: Nov. 11, 2003
Appl. No.: 09/982,468
Filed: Oct. 18, 2001

(30) Foreign Application Priority Data

Dec. 5, 2000 (IT) ..... MI2000A2631

(51) Int. Cl.
*C12P 13/06* (2006.01)
(52) U.S. Cl. ..... 435/116
(58) Field of Classification Search ..... 435/116
See application file for complete search history.

(56) References Cited

U.S. PATENT DOCUMENTS

| | | | | |
|---|---|---|---|---|
| 5,084,215 | A | 1/1992 | Kearns et al. | |
| 5,700,668 | A | 12/1997 | De Ferra et al. | |
| 5,833,858 | A | 11/1998 | Umeda et al. | |
| 6,492,146 | B1 * | 12/2002 | De Ferra et al. | 435/134 |
| 6,645,742 | B2 | 11/2003 | De Ferra et al. | |
| 2002/0103393 | A1 | 8/2002 | De Ferra et al. | |

FOREIGN PATENT DOCUMENTS

| | | | |
|---|---|---|---|
| BE | 827026 | A1 | 9/1975 |
| DE | 19917249 | | 9/2000 |
| EP | 0922707 | | 6/1999 |
| EP | 1048738 | A1 | 2/2000 |
| GB | 1504125 | A | 3/1978 |
| JP | 542917 | B2 | 2/1988 |

OTHER PUBLICATIONS

U.S. Reexamination Control No. 95/000,138 , Mar. 23, 2006.
Abidi, S.L., Separation procedures for phosphatidylserines, Journal of Chromatography B., 1998, vol. 717, pp. 279-293.
Radin, N. S., Extraction of Tissue Lipids with a Solvent of Low Toxicity, Methods in Enzymology, 1981, vol. 72, pp. 5-7.
Comfurius, P. et al., Enzymatic synthesis of phosphatidylserine on small scale by use of a one-phase system, Journal of Lipid Research, 1990, vol. 31, pp. 1719-1721.
Biochemistry, Third Edition, L. Stryer, 1989, p. 17.
Lehninger, A.L., Biochemistry, Second Edition, 1970, pp. 162.
Phospholipids Handbook Ed., G. Cevc, Dekker, Inc., 1993, p. 30 (Table 14).
Declaration of Lorenzo DeFerra under 37 CFR § 1.132 submitted as part of Patent Owner's Response of Jul. 24, 2006.
In Re Tanaka, Case No. 2010-1262 (Fed. Cir., Apr. 15, 2011).
BE827026, Pon, Sep. 22, 1975, Translation.
Translation of JP542917, Murakami et al., Feb. 17, 1988.
The Merck Index, Twelfth Edition, 1996; pp. xiv, 13-14, 802-803, 889-890.
Search Report for EP Application No. 0112 4577-6, dated Mar. 15, 2002.

* cited by examiner

*Primary Examiner* — Golam M M Shameem
(74) *Attorney, Agent, or Firm* — Caesar, Rivise, Bernstein, Cohen & Pokotilow, Ltd.

(57) ABSTRACT

The present invention relates to a purifying process for phosphatidylserine, the latter being prepared by trans-phosphatidylation of phosphatidylcholine with serine in presence of the enzyme D-phospholipase and containing as impurities hydrophilic compounds, proteins and inorganic salts.

26 Claims, No Drawings

PURIFYING PROCESS FOR PHOSPHATIDYLSERINE

Matter enclosed in heavy brackets [ ] appears in the original patent but forms no part of this reissue specification; matter printed in italics indicates the additions made by reissue.

FIELD OF THE INVENTION

The present invention relates to a purifying process for phosphatidylserine, a phospholipid which is useful in particular for the preparation of pharmaceutical compositions used in the treatment of involutional brain syndromes of various nature, but also in the preparation of particular liposome formulations and of dietetic compositions based on natural lecithins.

STATE OF THE ART

Phosphatidylserine is a phospholipid widely present in nature; it is one of the main components of cell membranes in animal organisms and is present in particularly large amounts in mammals' brain tissues. Medical literature mentions interesting properties of phosphatidylserine, among which the most significant relates to its effectiveness in improving mnemonic abilities.

The trans-phosphatidylation of phosphatidylcholine with serine in presence of the enzyme D-phospholipase according to the following scheme is the most convenient reaction for the industrial production of phosphatidylserine.

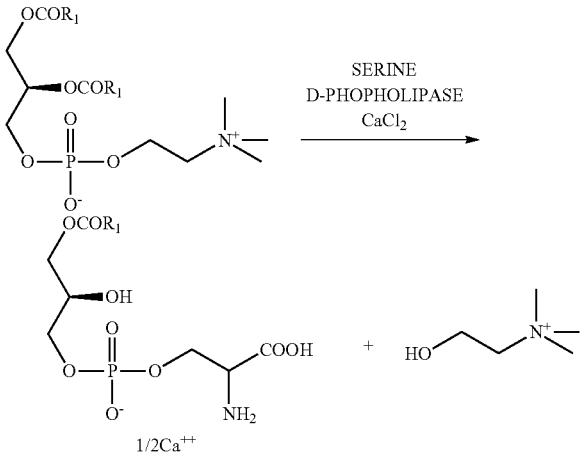

The reaction can be carried out both in an aqueous ambient, as described in the EP 1 048 738, and in a system containing beyond an aqueous phase also an organic solvent unmixable with water, preferably toluene; this second method is described in U.S. Pat. No. 5,700,668.

Whatever the method of trans-phosphatidylation used, the phosphatidylserine which can be isolated at the end of the process contains in any case large amounts of hydrophilic impurities, such as serine, choline and their salts which are present in the aqueous phase.

Another aspect which should be remarked is that, by measuring the enzymatic activity of the type D-phospholipase of the products according to the method described in related literature (Biotechn. Techn., 7, 795 (1993)), every gram of product is found to have about 2 international units of enzymatic activity. In compliance with the general request of strict criteria for purity, the removal of said impurities from the product is highly important.

The methods which are commonly used to remove hydrophilic substances from organic solutions of phospholipids have proved to be ineffective. As a matter of fact, by extracting a toluene solution of the phospholipid mixture obtained as described in U.S. Pat. No. 5,700,668, with the same amount of water, and then by separating the phases, it is found that the content of serine in the organic phase and the activity of D-phospholipase are practically unchanged with respect to the values found before the extraction with water.

Similarly, the elution of the same organic solution on a chromatographic column containing chromatography silica conditioned with toluene, in which the product elution is completed with toluene, results in a very small removal of serine and of the enzymatic activity from the phospholipid.

In another experiment the organic solution of phosphatidylserine to be purified because of serine is added with acetone: the precipitated product shows, after being analyzed, a ratio of serine to phosphatidylserine substantially unchanged with respect to the starting product.

Therefore, there is always the problem related to the availability of an effective purifying process for phosphatidylserines prepared by trans-phosphatidylation of phosphatidylcholine with serine in presence of the enzyme D-phospholipase, and containing as impurities hydrophilic compounds, proteins and inorganic salts.

SUMMARY OF THE INVENTION

The Applicant has now surprisingly found that hydrophilic impurities, proteins and inorganic salts can be successfully removed from a solution of phosphatidylserine in an organic solvent by extraction with water, provided that a polar organic solvent is added to the system.

The object of the present invention is therefore a purifying process for phosphatidylserines having formula (I)

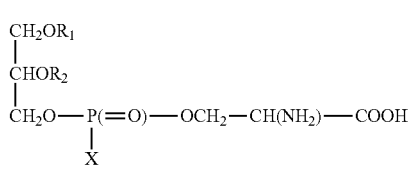

(I)

where $R_1$ e $R_2$, identical or different, are a $C_{10}$-$C_{30}$ acyl group;
X is OH or OM,
where M is chosen from the group of alkali metals, alkaline-earth metals, ammonium and alkyl ammonium,
and where the serine portion is in D, L or racemic form, and preferably in L form, comprising the extraction of said phosphatidylserines from a solution in a hydrocarbon solvent with a mixture of water and a polar organic solvent.

DETAILED DESCRIPTION OF THE INVENTION

In the specific case of phosphatidylserines prepared according to the description contained in U.S. Pat. No. 5,700,668 by trans-phosphatidylation in a two-phase system made of an aqueous phase and a toluene phase, the process according to the invention can be carried out directly on the toluene phase after separating the latter from the aqueous phase at the end of the reaction.

In the case of phosphatidylserines prepared following other methods, the purifying is process can be advantageously carried out by stirring the product in a mixture containing a hydrocarbon solvent, water and a polar organic solvent.

Also in this case the concerned phospholipid is present in the hydrocarbon phase, whereas hydrophilic impurities are to be found in the aqueous phase.

After separating the phases phosphatidylserine can be isolated using known methods such as precipitation with acetone.

According to the present process aromatic or aliphatic solvents can be used as hydrocarbon solvent; among aromatic solvents toluene or xilene are preferred; among aliphatic solvents it is preferable to use n-heptane, n-hexane or cyclohexane.

As polar organic solvent alcoholic solvents can be used, containing for instance 1 to 5 carbon atoms. According to preferred embodiments of the invention, said alcoholic solvent is chosen among secondary and tertiary alcohols; more preferably isopropanol is used.

The extraction according to the invention can be carried out at temperatures between 0 and 70° C., and preferably between 20 and 30° C.

The amount of hydrocarbon solvent is between 4 and 30 liters/kg of phospholipid to be purified, and preferably between 6 and 12 liters.

The volume ratio between water and hydrocarbon solvent is between 0.2 and 5, and preferably between 0.3 and 1. The volume ratio between polar organic solvent and hydrocarbon solvent is between 0.2 and 2, and preferably between 0.3 and 1.2.

The method described can be applied to phosphatidylserines with different acyclic chains and allows to purify both products deriving from the trans-phosphatidylation of phosphatidylcholines of natural origin such as soybean, rape or egg yolk, and phosphatidylcholines synthesized with fat acids, both saturated such as myristic acid, palmitic acid or stearic acid, and unsaturated such as oleic acid or linoleic acid.

The following examples merely aim at disclosing the present invention without limiting its object.

EXAMPLE 1

Preparation of Phosphatidylserine in a Two-phase System 400 g of a non de-oiled fraction of soybean lecithin, containing 32% of phosphatidylcholine and 50% of triglycerides, are charged into a flask together with 3 l of toluene. A solution of 22.7 g of calcium chloride, 27.6 g of trihydrated sodium acetate and 62.5 g of L-serine in 1.3 l of a solution of D-phospholipase with an activity of 3 KU/l is separately prepared. The solution is brought to pH=4.2 with acetic acid. The two solutions are united and kept under stirring at 25° C. for 8 hours. After filtration the phases are separated, one tenth of the toluene phase is concentrated under vacuum (the remaining part is used for the experiments described in examples 2, 3, 4, 5); the residue is added to 500 ml of acetone at room temperature. The product is filtered and dried, thus obtaining 27 g of a mixture of phospholipids with a content of phosphatidylserine of 50%.

TLC analysis (eluant: mixture of chloroform, methanol, water and 28% aqueous solution of ammonia 300:100:10:12; detector:ninhydrin) shows the presence of 1.5% of L-serine in the final product.

The presence of D-phospholipase in the product is determined with a method described in related literature (Biotechn. Techn., 7, 795 (1993)); an activity of 2.1 IU/g is found.

EXAMPLE 2

Purifying of Phosphatidylserine by Extraction with i-propanol and Water 330 ml of the toluene solution prepared as described in Example 1 are used. This solution is added with 240 ml of i-propanol and 150 ml of water. The whole is stirred at room temperature and settled, then the phases are separated. The toluene phase is concentrated and its residue is added under stirring to 500 ml of acetone.

The product has a content of L-serine of 0.3%. D-phospholipase is below the determination limit used in the method (0.1 IU/g).

EXAMPLE 3

Purifying of Phosphatidylserine by Extraction with i-propanol and Water in Different Ratios 330 ml of the toluene solution prepared as described in Example 1 are used. This solution is added with 150 ml of isopropanol and 240 ml of water. The whole is stirred at room temperature and settled, then the phases are separated. The toluene phase is concentrated and its residue is added under stirring to 500 ml of acetone.

The product has a content of L-serine of 0.2%. D-phospholipase is below the determination limit used in the method (0.1 IU/g).

EXAMPLE 4

Purifying of Phosphatidylserine by Extraction with Ethanol and Water 330 ml of the toluene solution prepared as described in Example 1 are used. This solution is added with 150 ml of ethanol and 150 ml of water. The whole is stirred at room temperature and settled, then the phases are separated. The toluene phase is concentrated and its residue is added under stirring to 500 ml of acetone.

The product has a content of L-serine of 0.2%. D-phospholipase is below the determination limit used in the method (0.1 IU/g).

EXAMPLE 5

Preparation of Phosphatidylserine in a Two-phase System Water/n-heptane and Purifying with i-propanol and Water 40 g of the same type of soybean lecithin used as raw material in Example 1 are charged into a flask together with 300 ml of n-heptane. A solution of 2.3 g of calcium chloride, 2.8 g of trihydrated sodium acetate and 6.3 g of L-serine in 0.13 l of a solution of D-phospholipase with an activity of 3 KU/l is separately prepared. The solution is brought to pH=4.2 with acetic acid. The two solutions are joined and kept under stirring at 25° C. for 24 hours. After filtration the phases are separated; the heptane phase is added with 150 ml of i-propanol and 150 ml of water. After stirring and settling the two phases are separated. The heptane phase is concentrated at low pressure. The residue is added to 500 ml of acetone at room temperature. The product is filtered and dried, thus obtaining 26.5 g of a mixture of phospholipids with a content of phosphatidylserine of 48%.

The product has a content of L-serine of 0.2%. D-phospholipase is below the determination limit of the method (0.1 IU/g).

EXAMPLE 6

Preparation of Phosphatidylserine by Trans-phosphatidylation in Absence of Organic Solvent 40 g of a mixture of phospholipids obtained by extraction with ethyl alcohol of soybean lecithin, whose main component is phosphatidylcholine (65%), are charged into a reparatory funnel together with a solution prepared by dissolving 60 g of calcium chloride in 800 ml of water; the mixture is kept under stirring at 25° C. for an hour. After 4 hours at rest 700 ml of aqueous phase are unloaded from the bottom tap. A solution containing 64 g of L-serine in 130 ml of 0.1 M acetate buffer at pH 4.5 is separately prepared. This solution is added with 300 mg of D-phospholipase in lyophilized form with an activity of 1.0 IU/mg. The resulting solution is added to the aqueous dispersion of phospholipids previously prepared.

The mixture is kept under stirring at 45° C. for 3 hours. The reaction product is separated by filtration; after being washed with water it weighs 60 g.

An aliquot is dried to determine serine and D-phospholipase. The result is that the content of serine is of 7% by weight and the activity of D-phospholipase is of 2 IU/g.

EXAMPLE 7

Purifying of Phosphatidylserine as Obtained in Example 6

5 g aliquots of the moist product obtained as described in Example 6 are used for purifying tests by dissolution in a mixture of solvents containing water, a hydrocarbon solvent (solvent 1) and an alcohol solvent (solvent 2).

In all tests phosphatidylserine is present, after stirring and settling, only in the hydrocarbon phase. The hydrocarbon phase is concentrated and precipitated from acetone. The dried products are analyzed by measuring the content of serine and the activity of D-phospholipase. The following Table 1 shows the purifying conditions used for phosphatidylserine and the amounts of serine and D-phospholipase which are present in the final product.

TABLE 1

| Purifying of phosphatidylserine | | | | | | |
|---|---|---|---|---|---|---|
| Test | 1 | 2 | 3 | 4 | 5 | 6 |
| Solvent 1 | n-heptane | n-heptane | n-heptane | n-heptane | n-heptane | n-heptane |
| Amount of Solvent 1 (ml) | 50 | 50 | 50 | 50 | 50 | 50 |
| Solvent 2 | methanol | i-propanol | i-propanol | i-propanol | i-propanol | i-propanol |
| Amount of solvent 2 (ml) | 60 | 15 | 15 | 30 | 30 | 50 |
| Amount of water (ml) | 25 | 15 | 30 | 15 | 30 | 40 |
| Serine in final product (%) | 1.0 | 0.8 | 0.2 | 1.3 | 0.3 | 0.6 |

TABLE 1-continued

| Purifying of phosphatidylserine | | | | | | |
|---|---|---|---|---|---|---|
| Test | 1 | 2 | 3 | 4 | 5 | 6 |
| D-phospholipase in final product (IU/g) | <0.1 | <0.1 | <0.1 | 0.1 | <0.1 | <0.1 |

EXAMPLE 8

Preparation and Purifying of Dioleoylphosphatidylserine (DOPS)

40 g of dioleoylphosphatidylcholine (DOPC) are charged into a flask together with 0.3 l of toluene. A solution of 2.3 g of calcium chloride, 2.8 g of trihydrated sodium acetate and 6.3 g of L-serine in 0.13 l of a solution of D-phospholipase with an activity of 3 KU/l is separately prepared. The solution is brought to pH=4.2 with acetic acid. The two solutions are joined and kept under stirring at 25° C. for 8 hours. The phases are then separated, the upper phase is added with 240 ml of i-propanol and 150 ml of water. The whole is stirred at room temperature and settled, then the phases are separated. The toluene phase is concentrated and its residue is added under stirring to 500 ml of acetone. The solid is filtered and dried under vacuum, thus obtaining 39 g of DOPS as calcium salt.

The product has a content of L-serine of 0.2%. D-phospholipase is below the determination limit used in the method (0.1 IU/g).

What is claimed is:

[1. Purifying process for phosphatidylserine having formula (I)

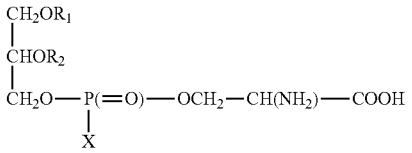

(I)

where $R_1$ and $R_2$, identical or different, are a $C_{10}$-$C_{30}$ acyl group; X is OH or OM, where M is chosen from the group of alkali metals, alkaline-earth metals, ammonium and alkyl ammonium, and where the serine portion is in D, L or racemic form, comprising the extraction of said phosphatidylserines from a solution in a hydrocarbon solvent chosen among aromatic and aliphatic hydrocarbon solvents, with a mixture of water and an alcohol solvent.]

[2. Process according to claim 1, in which said hydrocarbon solvent is selected from the group consisting of toluene, xylene, n-heptane, n-hexane and cyclohexane.]

[3. Process according to claim 1, in which said hydrocarbon solvent is used in an amount between 4 and 30 liters/kg of phosphatidylserine to be purified.]

[4. Process according to claim 3, in which said hydrocarbon solvent is used in an amount between 6 and 12 liters/kg of phosphatidylserine to be purified.]

[5. Process according to claim 1, in which said alcohol solvent is chosen among alcohols containing 1 to 5 carbon atoms.]

[6. Process according to claim 1, in which said alcohol solvent is chosen among secondary and tertiary alcohols.]

[7. Process according to claim 1, in which said alcohol solvent is isopropanol.]

[8. Process according to claim 1, in which said polar organic solvent is used in an amount between 0.2 and 2 liters/kg of hydrocarbon solvent used.]

[9. Process according to claim 8, in which said polar organic solvent is used in an amount between 0.3 and 1.2 liters/kg of hydrocarbon solvent used.]

[10. Process according to claim 1, in which the amount of water used is between 0.2 and 5 liters/kg of hydrocarbon solvent used.]

[11. Process according to claim 10, in which the amount of water used is between 0.3 and 1 liter/kg of hydrocarbon solvent used.]

[12. Process according to claim 1, in which said extraction is carried out at a temperature between 0 and 70° C.]

[13. Process according to claim 12, in which said extraction is carried out at a temperature between 20 and 30° C.]

[14. Process according to claim 1, in which said phosphatidylserines having formula (I) are prepared by trans-phosphatidylation of phosphatidylcholines of natural or synthetic origin.]

[15. Process according to claim 1, in which the said serine portion is in L form.]

[16. A purifying process for phosphatidylserine having formula (I)

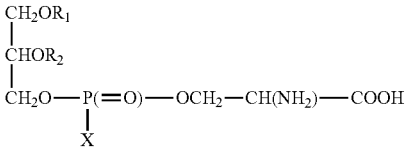

(I)

where $R_1$ and $R_2$, identical or different, are $C_{10}$-$C_{30}$ acyl groups;

X is OH or OM, where M is chosen from the group consisting of alkali-earth metals, ammonium and alkyl ammonium; and where the serine portion is in D, L or racemic form; which comprises stirring said phosphatidylserine in a mixture comprising water, an alcohol solvent, and a hydrocarbon solvent selected from the group consisting of aromatic and aliphatic hydrocarbon solvents.]

[17. The process of claim 16, in which said hydrogen solvent is selected from the group consisting of toluene, xylene, n-heptane, n-hexane and cyclohexane.]

[18. The process of claim 16, in which said hydrogen solvent is used in an amount between 4 and 30 liters per kilogram of phosphatidylserine to be purified.]

[19. The process of claim 18, in which said hydrogen solvent is used in an amount between 6 and 12 liters per kilogram of phosphatidylserine to be purified.]

[20. The process of claim 16, in which said alcohol solvent in an alcohol containing 1 to 5 carbon atoms.]

[21. The process of claim 16, in which said alcohol solvent is selected from the group consisting of secondary and tertiary alcohols.]

[22. The process of claim 16, in which said alcohol is isopropanol.]

[23. The process of claim 16, in which said polar organic solvent is used in an amount between 0.2 and 2 liters per kilogram of hydrocarbon solvent used.]

[24. The process of claim 23, in which said polar organic solvent is used in an amount between 0.3 and 1.2 liters per kilogram of hydrocarbon solvent used.]

[25. The process of claim 16, in which the amount of water used is between 0.2 and 5 liters per kilogram of hydrocarbon solvent used.]

[26. The process of claim 25, in which the amount of water used is between 0.3 and 1 liters per kilogram of hydrocarbon solvent used.]

[27. The process of claim 16, in which said stirring is carried out at a temperature between 0 and 70 ° C.]

[28. The process of claim 27, in which said stirring is carried out at a temperature between 20 and 30 ° C.]

[29. The process of claim 16, in which said phosphatidylserine is prepared by transphatidylation of phosphatidylcholines of natural or synthetic origin.]

[30. The process of claim 16, in which said serine portion is in L form.]

[31. The process of claim 1, further comprising precipitation of phosphatidylserine with acetone, after separation of the solvent phases.]

[32. The process of claim 16, further comprising precipitation of phosphatidylserine with acetone, after separation of the solvent phases.]

*33. Purifying process for phosphatidylserine having formula (I)*

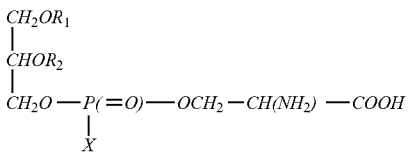

*(I)*

*where $R_1$ and $R_2$, identical or different, are a $C_{10}$-$C_{30}$ acyl group; X is OH or OM, where M is chosen from the group of alkali metals, alkaline-earth metals, ammonium and alkyl ammonium, and where the serine portion is in D, L or racemic form, which consists of:*

*a) stirring said phosphatidylserine in a mixture of water, an hydrocarbon solvent chosen among aromatic and aliphatic hydrocarbon solvents, and an alcohol solvent, selected from the group consisting of secondary alcohols containing 3 to 5 carbon atoms;*

*b) settling the mixture; and*

*c) isolating phosphatidylserine after separation of the hydrocarbon phase and the aqueous phase;*

*wherein said phosphatidylserine is prepared by transphosphatidylation of phosphatidylcholine of natural or synthetic origin with serine in the presence of D-phospholipase, and further wherein said purifying process removes the phospholipase and serine which remain in the aqueous phase.*

*34. Process according to claim 33, in which said hydrocarbon solvent is selected from the group consisting of toluene, n-heptane, n-hexane and cyclohexane.*

*35. Process according to claim 33, in which said hydrocarbon solvent is used in an amount between 4 and 30 liters/kg of phosphatidylserine to be purified.*

*36. Process according to claim 35, in which said hydrocarbon solvent is used in an amount between 6 and 12 liters/kg of phosphatidylserine to be purified.*

*37. Process according to claim 33, in which said hydrocarbon solvent is n-heptane.*

*38. Process according to claim 33, in which said alcohol solvent is isopropanol.*

*39. Process according to claim 33, in which said alcohol solvent is used in an amount between 0.2 and 2 liters/kg of hydrocarbon solvent used.*

*40. Process according to claim 35, in which said alcohol solvent is used in an amount between 0.3 and 1.2 liters/kg of hydrocarbon solvent used.*

*41. Process according to claim 33, in which the amount of water used is between 0.2 and 5 liters/kg of hydrocarbon solvent used.*

*42. Process according to claim 41, in which the amount of water used is between 0.3 and 1 liter/kg of hydrocarbon solvent used.*

*43. Process according to claim 33, in which said purification process is carried out at a temperature between 0 and 70° C.*

*44. Process according to claim 43, in which said purification process is carried out at a temperature between 20 and 30° C.*

*45. Process according to claim 33, wherein isolation of said phosphatidylserine includes precipitation with acetone.*

*46. A purifying process according to claim 33 which consists of:*

*a) stirring a solution of phosphatidylserine in a hydrocarbon solution chosen among aromatic and aliphatic hydrocarbon solvents with a mixture of water, and an alcohol solvent selected from the group consisting of secondary alcohols containing 3 to 5 carbon atoms;*

*b) settling the mixture; and*

*c) isolating phosphatidylserine after separation of the hydrocarbon phase and the aqueous phase;*

*wherein said solution in a hydrocarbon solvent of phosphatidylserine is prepared by transphosphatidylation of phosphatidylcholine of natural or synthetic origin with serine in the presence of D-phospholipase in a two-phase system, and further wherein said purifying process removes the phospholipase and serine which remain in the aqueous phase.*

*47. The process of claim 46, in which said hydrocarbon solvent is selected from the group consisting of toluene, n-heptane, n-hexane and cyclohexane.*

*48. The process of claim 46, in which said hydrocarbon solvent is used in an amount between 4 and 30 liters per kilogram of phosphatidylserine to be purified.*

*49. The process of claim 48, in which said hydrocarbon solvent is used in an amount between 6 and 12 liters per kilogram of phosphatidylserine to be purified.*

*50. The process of claim 46, in which said hydrocarbon solvent is n-heptane.*

*51. The process of claim 46, in which said alcohol solvent is isopropanol.*

*52. The process of claim 46, in which said alcohol solvent is used in an amount between 0.2 and 2 liters per kilogram of hydrocarbon solvent used.*

*53. The process of claim 52, in which said alcohol solvent is used in an amount between 0.3 and 1.2 liters per kilogram of hydrocarbon solvent used.*

*54. The process of claim 46, in which the amount of water used is between 0.2 and 5 liters per kilogram of hydrocarbon solvent used.*

*55. The process of claim 54, in which the amount of water used is between 0.3 and 1 liters per kilogram of hydrocarbon solvent used.*

*56. The process of claim 46, in which said purification process is carried out at a temperature between 0 and 70° C.*

*57. The process of claim 56, in which said purification process is carried out at a temperature between 20 and 30° C.*

*58. The process of claim 46, wherein isolation of said phosphatidylserine includes precipitation with acetone.*

* * * * *